(12) United States Patent
Gomez et al.

(10) Patent No.: US 11,491,269 B2
(45) Date of Patent: Nov. 8, 2022

(54) ARTERIAL CHAMBERS FOR HEMODIALYSIS AND RELATED SYSTEMS AND TUBING SETS

(71) Applicant: Fresenius Medical Care Holdings, Inc., Waltham, MA (US)

(72) Inventors: Irving Uziel Hernandez Gomez, Hidalgo, TX (US); Juan Arturo Montecillo Juárez, Reynosa (MX); Diego Suarez del Real Pena, Mission, TX (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 296 days.

(21) Appl. No.: 16/747,771

(22) Filed: Jan. 21, 2020

(65) Prior Publication Data

US 2021/0220538 A1      Jul. 22, 2021

(51) Int. Cl.
| | |
|---|---|
| *A61M 1/16* | (2006.01) |
| *A61M 1/26* | (2006.01) |
| *A61M 1/36* | (2006.01) |
| *A61B 5/15* | (2006.01) |

(52) U.S. Cl.
CPC ..... *A61M 1/1621* (2014.02); *A61B 5/150992* (2013.01); *A61M 1/267* (2014.02); *A61M 1/3627* (2013.01); *A61M 1/3672* (2013.01); *A61M 2205/3331* (2013.01)

(58) Field of Classification Search
CPC .......... A61B 5/150992; A61M 1/1621; A61M 1/267; A61M 1/3627; A61M 1/3672; A61M 2205/3331
See application file for complete search history.

(56) References Cited

U.S. PATENT DOCUMENTS

| | | | |
|---|---|---|---|
| 4,666,598 A | 5/1987 | Heath et al. | |
| 5,328,461 A | 7/1994 | Utterberg | |
| 5,391,150 A | 2/1995 | Richmond | |
| 5,503,801 A | 4/1996 | Brugger | |
| 5,520,640 A * | 5/1996 | Utterberg | ............ A61M 1/3627 604/80 |
| 5,645,538 A | 7/1997 | Richmond | |
| 5,693,008 A | 12/1997 | Brugger et al. | |

(Continued)

FOREIGN PATENT DOCUMENTS

EP          0568275 A2      11/1993

OTHER PUBLICATIONS

International Search Report and Written Opinion received for PCT Application Serial No. PCT/US2021/013357 dated Apr. 9, 2021, 8 pages.

*Primary Examiner* — Dirk R Bass
(74) *Attorney, Agent, or Firm* — FisherBroyles, LLP

(57) ABSTRACT

The disclosed arterial chambers for hemodialysis may include a cap with a blood inlet port for conveying an intended patient's blood into the arterial chamber, an auxiliary port configured to provide fluid access to the arterial chamber, and a needleless access port configured to couple to a needleless syringe. The needleless access port may be configured for administering a substance to an interior of the arterial chamber from the needleless syringe and/or for withdrawing blood from the interior of the arterial chamber into the needleless syringe. Various tubing sets, hemodialysis systems, and other components, systems, and methods are also disclosed.

18 Claims, 7 Drawing Sheets

(56) References Cited

U.S. PATENT DOCUMENTS

| | | | |
|---|---|---|---|
| 5,772,624 A * | 6/1998 | Utterberg | A61M 1/1682 210/636 |
| 5,848,994 A | 12/1998 | Richmond | |
| 5,876,366 A | 3/1999 | Dykstra et al. | |
| 5,983,947 A | 11/1999 | Utterberg | |
| 6,179,823 B1 | 1/2001 | Niedospial, Jr. | |
| 6,491,668 B1 | 12/2002 | Paradis | |
| 6,514,225 B1 | 2/2003 | Utterberg et al. | |
| 6,855,138 B2 | 2/2005 | Tsai | |
| 2001/0010802 A1 * | 8/2001 | Tamari | A61M 1/3667 422/41 |
| 2005/0059952 A1 | 3/2005 | Giuliano et al. | |
| 2006/0017339 A1 | 1/2006 | Chordia et al. | |
| 2009/0095679 A1 * | 4/2009 | Demers | A61M 1/3609 210/646 |
| 2010/0013095 A1 | 1/2010 | Hada et al. | |
| 2017/0025250 A1 | 1/2017 | Carragher et al. | |
| 2018/0018555 A1 | 1/2018 | Wong et al. | |

* cited by examiner

ARTERIAL CHAMBERS FOR HEMODIALYSIS AND RELATED SYSTEMS AND TUBING SETS

BACKGROUND

Dialysis is a treatment for patients who have experienced kidney failure. In individuals with fully functioning kidneys, the kidneys remove excess water and nitrogen waste materials (e.g., in the form of urea and creatinine) from the blood and pass these materials to the bladder for expulsion from the body. Without properly functioning kidneys, a patient may not be able to maintain proper blood pH level and pressure. Dialysis may replace or supplement the kidneys' function in such patients.

Hemodialysis is a type of dialysis in which blood is drawn from a patient via an artery, passed through a dialyzer, and returned to the patient via a vein. The dialyzer includes a semi-permeable membrane with the patient's blood passing along one side of the membrane and a dialysate solution on the other side of the membrane. The dialysate solution typically includes an acid and bicarbonate in purified water. Waste products pass from the blood to the dialysate solution and treated (e.g., cleaned) blood can pass out of the dialyzer and back to the patient's circulatory system. The blood is delivered to the dialyzer through tubing and a variety of other components. For example, the blood may pass through a pump for moving the blood through tubing, one or more drip chambers used to ensure no air bubbles are present in the blood passing through the dialyzer or returned to the patient, a pressure sensor, an anti-clotting system, a heater, a blood volume monitor, and potentially various other sensors and systems.

In some conventional dialysis machines, a port is provided along the tubing for sampling the patient's blood and/or for administering medication, fluids, or other products to the blood as it passes through the dialysis machine. Typically, a medical professional can administer medication to the patient through such a port from a syringe by removing a cap on the port, piercing a resealable membrane of the port with a needle shaft, releasing a clamp between the port and the tubing, injecting the medication into the tubing, securing the clamp, withdrawing the needle shaft from the resealable membrane, and replacing the clamp. Needle usage generally requires careful handling and proper disposal techniques. Needle usage is also associated with a risk of accidental pricks and potential cross-contamination.

BRIEF DESCRIPTION OF THE DRAWINGS

The accompanying drawings illustrate a number of example embodiments and are a part of the specification. Together with the following description, these drawings demonstrate and explain various principles of the present disclosure.

Figure 1:
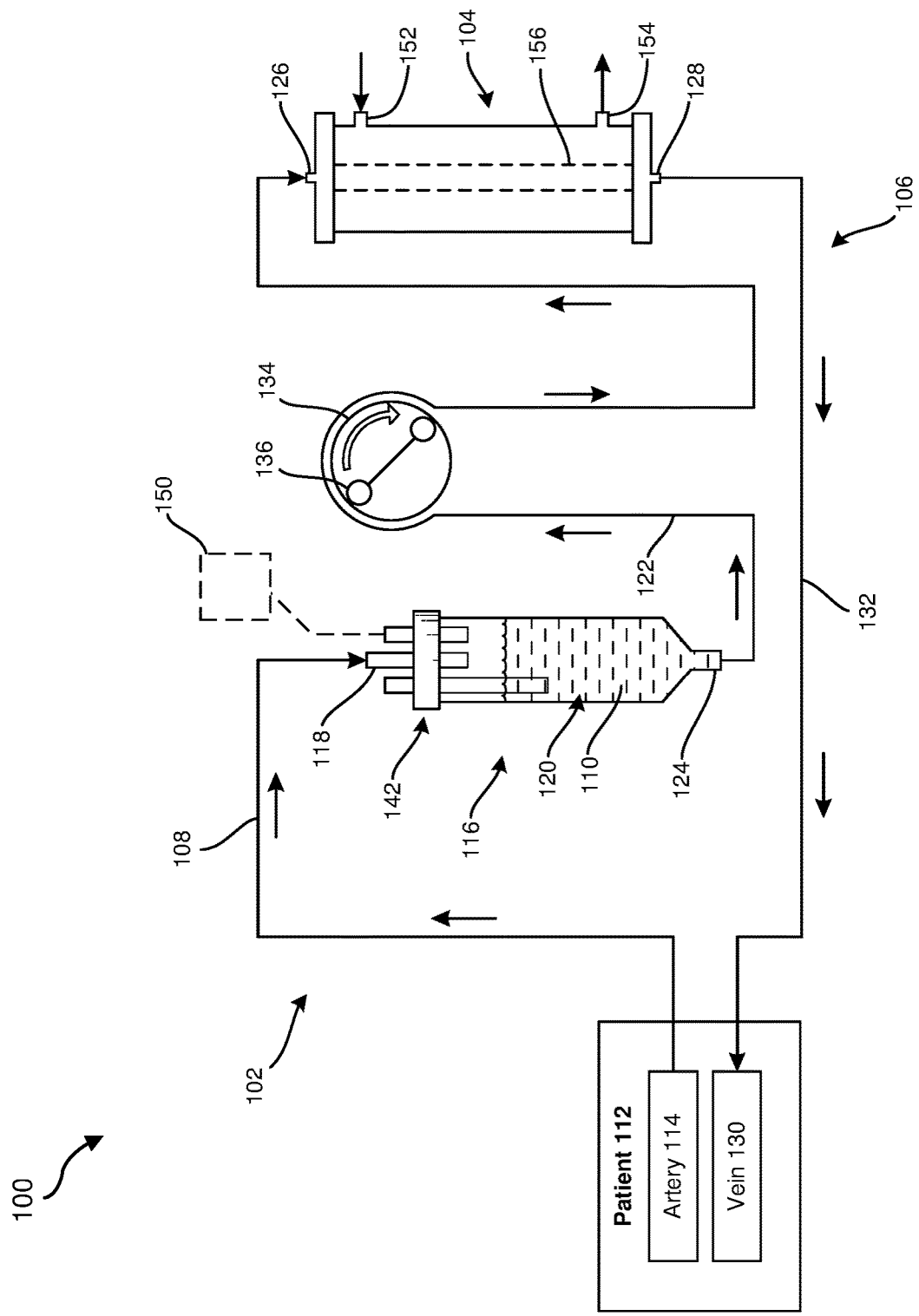
FIG. 1 is a schematic diagram of a hemodialysis system with a pre-pump arterial chamber, according to at least one embodiment of the present disclosure.

Throughout the drawings, identical reference characters and descriptions indicate similar, but not necessarily identical, elements. While the example embodiments described herein are susceptible to various modifications and alternative forms, specific embodiments have been shown by way of example in the drawings and will be described in detail herein. However, the example embodiments described herein are not intended to be limited to the particular forms disclosed. Rather, the present disclosure covers all modifications, equivalents, and alternatives falling within the scope of the appended claims.

DETAILED DESCRIPTION OF EXAMPLE EMBODIMENTS

The present disclosure is generally directed to arterial chambers (e.g., arterial drip chambers) for hemodialysis, hemodialysis systems, and arterial tubing sets for hemodialysis systems. As will be explained in further detail below, arterial chambers according to some embodiments may include a cap that has a blood inlet port, a needleless access port, and an auxiliary port. The needleless access port may be provided as an administration port and/or as a sampling port for use with a needleless syringe. The auxiliary port may be provided for use with an auxiliary element, such as a saline solution source, an anticoagulant source, a pressure sensor, an air release valve, and/or a medication source. The three ports in the cap of the arterial chambers may facilitate various uses and configurations in connection with hemodialysis. For example, the needleless access port may reduce the time and skill required for taking a sample of the patient's blood and/or for administering a medical substance to the patient's blood. In addition, the risk of needle hazards may be reduced or eliminated.

Features from any of the embodiments described herein may be used in combination with one another in accordance with the general principles described herein. These and other embodiments, features, and advantages will be more fully understood upon reading the following detailed description in conjunction with the accompanying drawings and claims.

Figure 2:
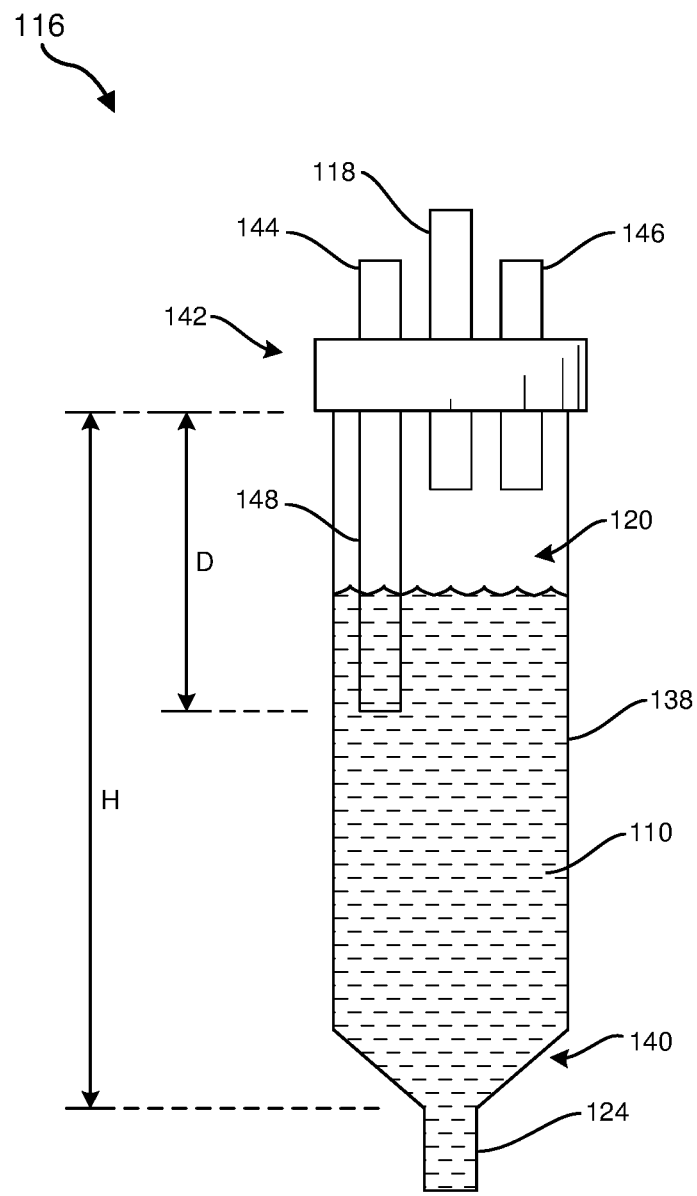
FIG. 2 is a detailed side view of the arterial chamber of FIG. 1.
Figure 3:
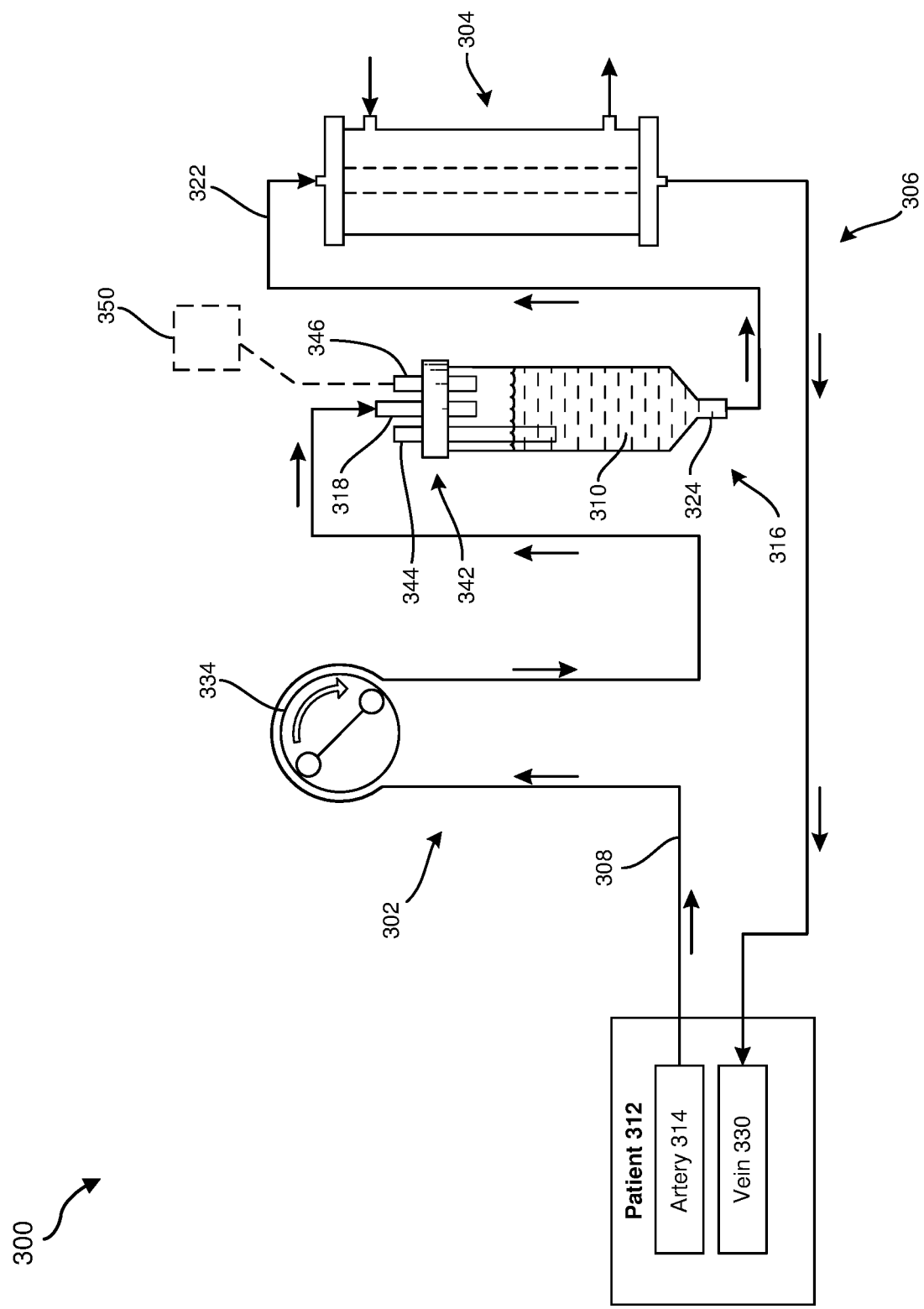
FIG. 3 is a schematic diagram of a hemodialysis system with a post-pump arterial chamber, according to at least one additional embodiment of the present disclosure.

The following will provide, with reference to FIGS. 1 and 3, detailed descriptions of hemodialysis systems according to embodiments of the present disclosure. With reference to FIGS. 2 and 4-6B, the following will provide detailed descriptions of arterial chambers (e.g., arterial drip chambers) and components thereof for use with hemodialysis systems. With reference to FIG. 7, the following will provide detailed descriptions of example methods for fluidically accessing an arterial chamber of a hemodialysis system.

FIG. 1 is a schematic diagram of a hemodialysis system 100, according to at least one embodiment of the present disclosure. The hemodialysis system 100 may include an arterial-side tubing set 102, a dialyzer 104, and a venous-side tubing set 106.

The arterial-side tubing set 102 may include a first flexible tube 108 that may be configured to receive blood 110 from a patient 112 (e.g., from an artery 114 of the patient 112). The arterial-side tubing set 102 may also include an arterial chamber 116 (e.g., a drip chamber) with a blood inlet port 118 fluidically coupled to the first flexible tube 108. Thus, the blood inlet port 118 may be configured to receive the blood 110 from the first flexible tube 108 and to convey the blood 110 into an interior 120 of the arterial chamber 116. The arterial-side tubing set 102 may also include a second flexible tube 122. One end of the second flexible tube 122 may be fluidically coupled to a blood outlet port 124 of the arterial chamber 116 and an opposing end of the second flexible tube 122 may be fluidically coupled to a dialyzer blood inlet 126 of the dialyzer 104. In some embodiments, the arterial-side tubing set 102 may include additional components, such as one or more fluid access ports, pressure sensors, line clamps, etc.

In some examples, relational terms, such as "first," "second," "top," "bottom," etc., may be used for clarity and convenience in understanding the disclosure and accompanying drawings and may not necessarily connote or depend on any specific preference, orientation, or order, except where the context clearly indicates otherwise.

The venous-side tubing set 106 may include at least one third flexible tube 132 fluidically coupled to a dialyzer blood outlet 128 of the dialyzer 104. The third flexible tube 132 may be configured to receive the blood 110 from the dialyzer 104 and to convey the blood 110 (e.g., cleaned blood) back to the patient 112, such as to a vein 130 of the patient 112. In some embodiments, the venous-side tubing set 106 may include additional components, such as one or more fluid access ports, pressure sensors, line clamps, venous chambers (e.g., a venous chamber the same as or similar to the arterial chamber 116), etc.

Each of the first flexible tube 108, second flexible tube 122, and third flexible tube 132 may include (e.g., may be formed of) a medical grade polymer material with hemocompatibility, such as polyvinylchloride ("PVC"), silicone, polytetrafluoroethylene ("PTFE"), etc. The flexible tubes 108, 122, 132 may be substantially transparent to visible light, such as to facilitate identification of flow of the blood 110, potential clotting, and/or potential air bubbles. Each of the flexible tubes 108, 122, 132 may include a single section of continuous tubing or may include two or more connected segments of tubing.

In some examples, the term "substantially" in reference to a given parameter, property, or condition may mean and include to a degree that one of ordinary skill in the art would understand that the given parameter, property, or condition is met within a small degree of variance, such as within acceptable manufacturing tolerances. By way of example, depending on the particular parameter, property, or condition that is substantially met, the parameter, property, or condition may be at least 90% met, at least 95% met, or even at least 99% met.

A pump 134 may be positioned and configured to force the blood 110 through the arterial-side tubing set 102, the dialyzer 104, and the venous-side tubing set 106. As illustrated in FIG. 1, the pump 134 may be positioned downstream from the arterial chamber 116 and may be operatively coupled to the second flexible tube 122. In this configuration, the arterial chamber 116 may be in a pre-pump position. The pump 134 may apply (e.g., through a portion of the second flexible tube 122) a negative pressure to the blood outlet port 124 of the arterial chamber 116 to draw the blood 110 through the arterial chamber 116 from the blood inlet port 118 to the blood outlet port 124. In some embodiments, the pump 134 may be a roller-type pump that includes one or more rollers 136 for rolling along a section of the second flexible tube 122 to progressively compress the second flexible tube 122 and to draw the blood 110 through the arterial-side tubing set 102 (and ultimately also through the dialyzer 104 and the venous-side tubing set 106) at a controlled flow rate. In some examples, the section of the second flexible tube 122 that interacts with the pump 134 may have a larger diameter than other sections of the second flexible tube 122. In addition, the section of the second flexible tube 122 that interacts with the pump 134 may be formed of a different material relative to other sections of the second flexible tube 122, such as to exhibit mechanical properties that are suitable for interacting with the pump 134 (e.g., for being repeatedly compressed by the rollers 136).

FIG. 2 is a detailed side view of the arterial chamber 116. Referring to FIGS. 1 and 2, the arterial chamber 116 may include a housing 138 defining the interior 120 of the arterial chamber 116. The housing 138 may be configured to collect air from the blood 110 of the patient 112 as the blood 110 passes through the housing 138. In some examples, the housing 138 may have a substantially cylindrical shape. A narrowing portion 140 may be located adjacent to the blood outlet port 124. A cap 142 may be coupled to (e.g., screwed to, press-fit to, and/or adhered to, etc.) the housing 138. The blood inlet port 118 may be coupled to (e.g., rigidly coupled to, screwed to, adhered to, and/or integrally formed with, etc.) the cap 142. A needleless access port 144 and an auxiliary port 146 may also be coupled to (e.g., rigidly coupled to, screwed to, adhered to, and/or integrally formed with, etc.) the cap 142. Thus, the cap 142 may include at least three ports, namely the blood inlet port 118, the needleless access port 144, and the auxiliary port 146.

As noted above, the blood inlet port 118 may be configured for connection to the first flexible tube 108 of the arterial-side tubing set 102. The needleless access port 144 may be configured to couple to a needleless syringe for at least one of administering a substance (e.g., a medication, a saline solution, a hydrating solution, a blood treatment, etc.) to the interior 120 of the housing 138 and/or withdrawing (e.g., sampling) the blood 110 of the patient 112 from the interior 120 of the housing 138. The needleless access port 144 may be resealable, such that the needleless access port 144 may close upon decoupling of the needleless syringe from the needleless access port 144.

In some embodiments, such as for using the needleless access port 144 as a sampling port, a conduit 148 in fluid communication with the needleless access port 144 may extend from the cap 142 into the interior 120 of the housing 138 a sufficient distance D to be at least partially submerged in the blood 110 within the arterial chamber 116 during expected operation of the hemodialysis system 100. For example, the housing 138 may have a height H between the cap 142 and the blood outlet port 124, and the conduit 148 may extend from the cap 142 into the interior 120 of the housing 138 the distance D that is sufficient to reach the blood 110 within the housing 138 during typical use. By way of example and not limitation, the distance D may be at least 25% of the height H, such as at least 50% of the height H. Thus, a portion of the blood 110 may be drawn into a needleless syringe coupled to the needleless access port 144 through the conduit 148 and the needleless access port 144.

The auxiliary port 146 may also be configured to provide fluid access to the interior 120 of the housing 138 for a variety of potential purposes. For example, the auxiliary port 146 may be configured as a sampling port and/or for connecting an auxiliary element 150 (FIG. 1) to the arterial chamber 116. By way of example and not limitation, the auxiliary element 150 may be a saline solution source, an anticoagulant (e.g., heparin) source, a pressure sensor, an air release valve, a medication source, etc. In some embodiments, as illustrated in FIGS. 1 and 2, respective conduits may also extend into the interior 120 of the housing 138 from at least one of the blood inlet port 118 and/or the auxiliary port 146.

Although the arterial chamber 116 is illustrated in FIGS. 1 and 2 as a drip chamber with the blood inlet port 118 at a gravitational top of the arterial chamber 116 and the blood outlet port 124 at a gravitational bottom of the arterial chamber 116, the present disclosure is not so limited. In additional embodiments, the arterial chamber 116 may be configured to receive the blood 110 through an inlet port at a gravitational bottom of the arterial chamber 116 and to convey the blood 110 to an outlet port at a gravitational top of the arterial chamber 116. In further embodiments, both the inlet port and the outlet port may be positioned at a gravitational bottom of the arterial chamber 116. In yet further embodiments, one or both of the inlet port and/or the outlet port may be positioned at a gravitational side of the arterial chamber 116. In addition, the cap 142 (including the blood inlet port 118, the needleless access port 144, the auxiliary port 146, and/or the blood outlet port 124) may be positioned at a gravitational top of the arterial chamber 116 as illustrated in FIGS. 1 and 2, at a gravitational bottom of the arterial chamber 116, or at a gravitational side of the arterial chamber 116.

Referring again to FIG. 1, the dialyzer 104 may include the dialyzer blood inlet 126, the dialyzer blood outlet 128, a dialysate inlet 152, a dialysate outlet 154, and a semi-permeable membrane 156. As noted above, the dialyzer blood inlet 126 may be fluidically coupled to the arterial-side tubing set 102 for receiving the blood 110 from the patient 112 and the dialyzer blood outlet 128 may be fluidically coupled to the venous-side tubing set 106 for returning the blood 110 (e.g., cleaned blood) to the patient 112. The dialysate inlet 152 may be configured for flowing a dialysate solution into the dialyzer 104 and the dialysate outlet 154 may be configured for flowing the dialysate solution and waste products from the blood 110 out of the dialyzer 104. The semi-permeable membrane 156 may be positioned within the dialyzer 104 and may physically separate at least a portion of the blood 110 (e.g., blood cells) from the dialysate solution while allowing waste products (e.g., urea, etc.) from the blood 110 to pass through the semi-permeable membrane 156 to be withdrawn from the dialyzer 104 with the dialysate solution through the dialysate outlet 154.

FIG. 3 is a schematic diagram of a hemodialysis system 300 with a post-pump arterial chamber 316, according to at least one additional embodiment of the present disclosure. In some respects, the hemodialysis system 300 may be similar to the hemodialysis system 100 described above with reference to FIG. 1. For example, the hemodialysis system 300 may include an arterial-side tubing set 302 for receiving blood 310 from a patient 312 (e.g., from an artery 314 of the patient 312), a dialyzer 304 for withdrawing waste products from the blood 310, and a venous-side tubing set 306 for returning the blood 310 to the patient 312 (e.g., to a vein 330 of the patient 312). The arterial-side tubing set 302 may include a first flexible tube 308, the arterial chamber 316, and a second flexible tube 322. The arterial chamber 316 may be the same as or similar to the arterial chamber 116 described above with reference to FIG. 1. For example, the arterial chamber 316 may include a cap 342 with a blood inlet port 318, a needleless access port 344, and an auxiliary port 346 (such as for connecting to an auxiliary element 350). The arterial chamber 316 may also include a blood outlet port 324.

As illustrated in FIG. 3, the hemodialysis system 300 may include a pump 334 operatively coupled to the arterial-side tubing set 302 to force the blood 310 of the patient 312 through the arterial-side tubing set 302, the dialyzer 304, and the venous-side tubing set 306. The pump 334 may be the same as or similar to the pump 134 described above with reference to FIG. 1. However, as illustrated in FIG. 3, the pump 334 may be located upstream from the arterial chamber 316 and may be operatively coupled to the first flexible tube 308. Operation of the pump 334 may apply (e.g., through a portion of the first flexible tube 308) a positive pressure to the blood inlet port 318 of the arterial chamber 316 to force the blood 310 through the arterial chamber 316 from the blood inlet port 318 to the blood outlet port 324 at a controlled flow rate.

Figure 4:
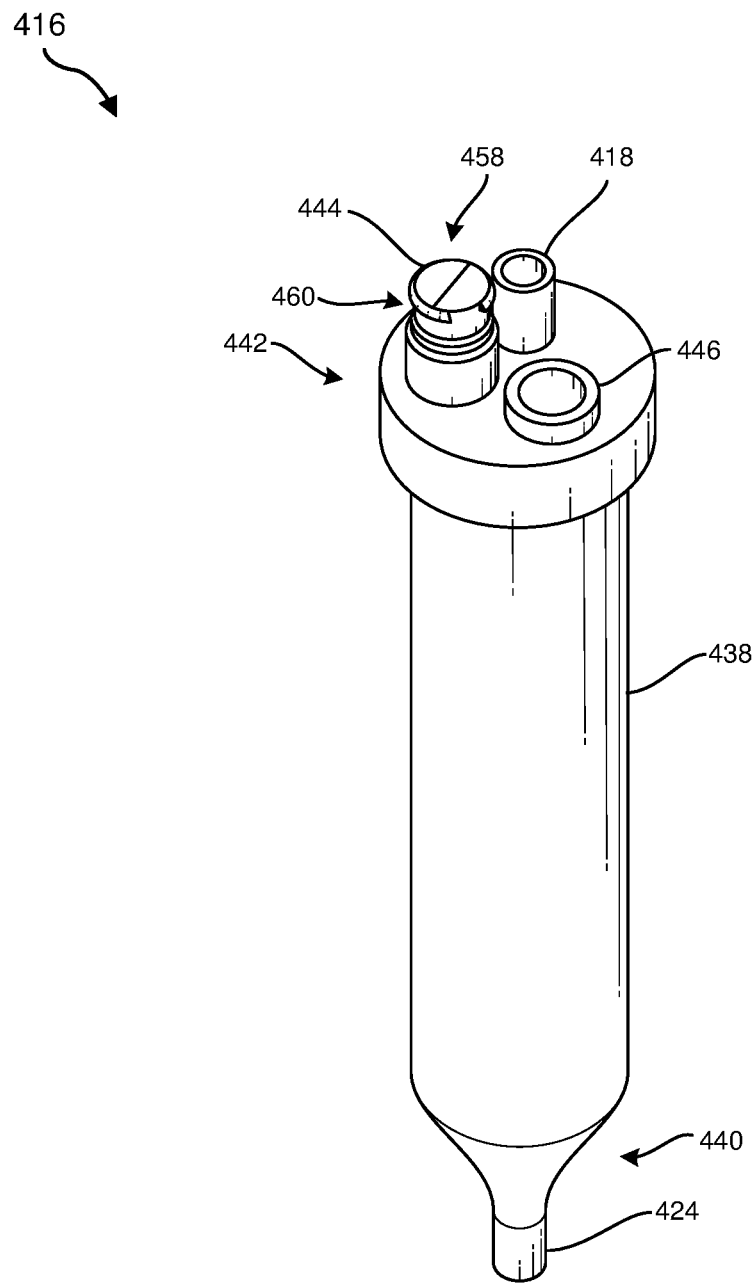
FIG. 4 is a perspective view of an arterial chamber, according to at least one additional embodiment of the present disclosure.

FIG. 4 is a perspective view of an arterial chamber 416, according to at least one additional embodiment of the present disclosure. In some respects, the arterial chamber 416 may be similar to the arterial chamber 116 described above with reference to FIGS. 1 and 2. For example, the arterial chamber 416 may include a blood outlet port 424 and a cap 442 that may include a blood inlet port 418, a needleless access port 444, and an auxiliary port 446. The arterial chamber 416 may also include a housing 438 and a narrowing portion 440 adjacent to the blood outlet port 424.

As illustrated in FIG. 4, the blood inlet port 418, needleless access port 444, and auxiliary port 446 may have a variety of configurations. For example, each of the blood inlet port 418, needleless access port 444, and auxiliary port 446 may have a different or a same size (e.g., diameter, height, etc.) and may include a different or a same connector type. In the embodiment shown in FIG. 4, the blood inlet port 418 and auxiliary port 446 may each include an interior sized and shaped for receiving a respective tube via an interference fit, for example. However, the present disclosure is not so limited. In additional embodiments, the blood inlet port 418 and/or the auxiliary port 446 may include a Luer connection element, a rotatable connector, a clamp connector, or a spike connector, etc.

The needleless access port 444 may include a split septum 458 to enable repeated coupling and decoupling of a needleless syringe while maintaining a fluid seal in a closed position. As shown in FIG. 4, the split septum 458 may include a single slit, which may open when a shaft of a needleless syringe is coupled to (e.g., plunged into) the split septum 458 and which may close when the shaft is decoupled from (e.g., withdrawn from) the split septum 458. The split septum 458 may include a resilient material (e.g., an elastomer) that is configured to return to its original, closed state after a needleless syringe is decoupled from the split septum 458. In some embodiments, the needleless access port 444 may include a Luer connection element 460 for coupling a Luer fitting of the needleless syringe to the needleless access port 444. Although the needleless access port 444 is illustrated in FIG. 4 to include a split septum 458, the present disclosure is not so limited. For example, other conventional needleless access port configurations may be used for the needleless access port 444.

As shown in FIG. 4, the blood inlet port 418, needleless access port 444, and auxiliary port 446 may be positioned in the cap 442 in a triangular arrangement. For some applications, this triangular arrangement may facilitate access to each of the blood inlet port 418, needleless access port 444, and auxiliary port 446, such as to couple or decouple components with these ports 418, 444, 446, respectively. Alternatively, in some embodiments the blood inlet port 418, needleless access port 444, and auxiliary port 446 may be positioned in the cap 442 in other arrangements, such as in a linear arrangement.

Figure 5:
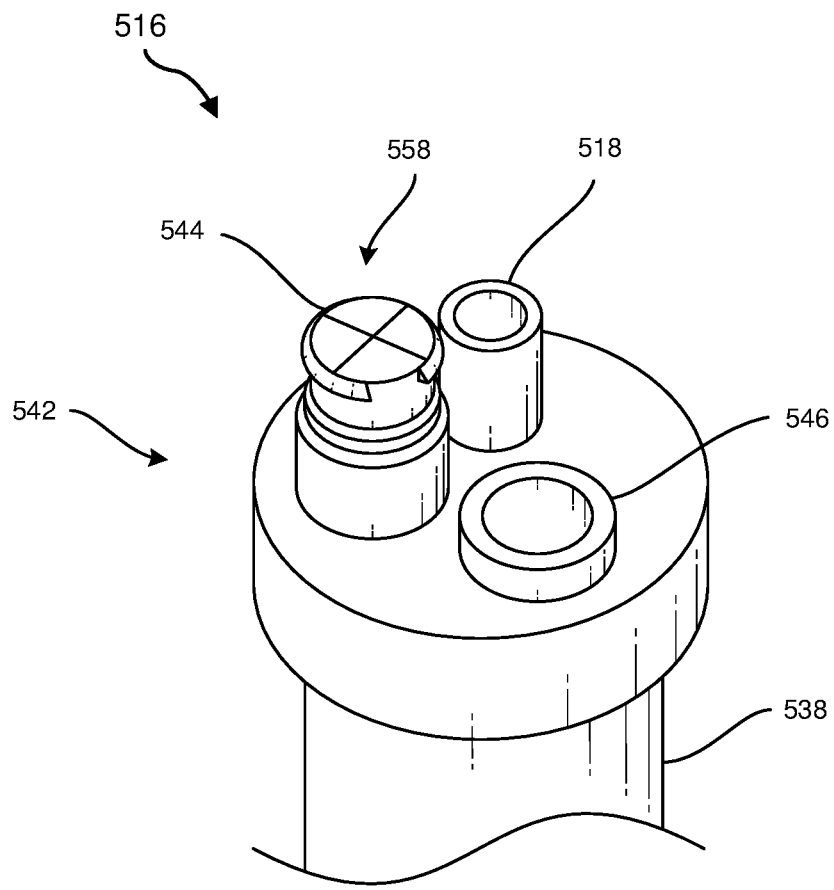
FIG. 5 is a perspective view of a cap of an arterial chamber, according to at least one other embodiment of the present disclosure.
Figure 6B:
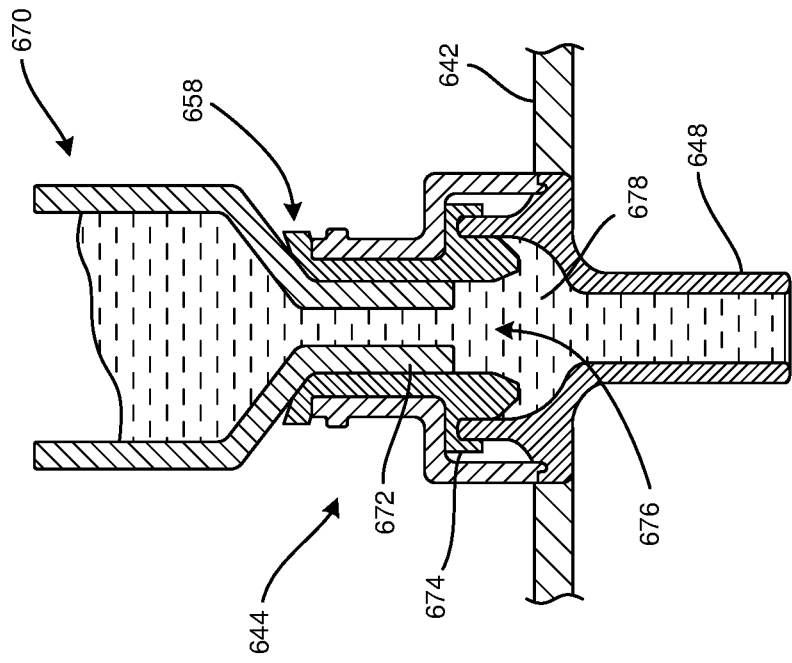
FIG. 6B is a side cross-sectional view of the needleless syringe and needleless access port of FIG. 6A, with a shaft of the needleless syringe inserted into the needleless access port and the needleless access port in an open position.

FIG. 5 is a perspective view of a cap 542 of an arterial chamber 516, according to at least one other embodiment. In some respects, the cap 542 and the arterial chamber 516 may be similar to the caps 142, 342, 442 and the arterial chambers 116, 316, 416 described above. For example, the cap 542 may include a blood inlet port 518, a needleless access port 544, and an auxiliary port 546. The arterial chamber 516 may include a housing 538 for containing blood from a patient and for collecting air from the blood. The needleless access port 544 may include a split septum 558.

As illustrated in FIG. 5, the blood inlet port 518, the needleless access port 544, and the auxiliary port 546 may each be rigidly coupled to the cap 542. For example, each of these ports 518, 544, 546 may be screwed, press-fit, adhered to, and/or formed integrally with the cap 542. Thus, there may be no flexible tubing between each of the ports 518, 544, 546 and the cap 542. In addition, the split septum 558 may include two transverse slits to enable a shaft of a needleless syringe to be coupled to the split septum 558. The two transverse slits may facilitate insertion of the shaft, such as at different angles of approach. Accordingly, a variety of different configurations are possible for needleless access ports of the present disclosure.

Figure 6A:
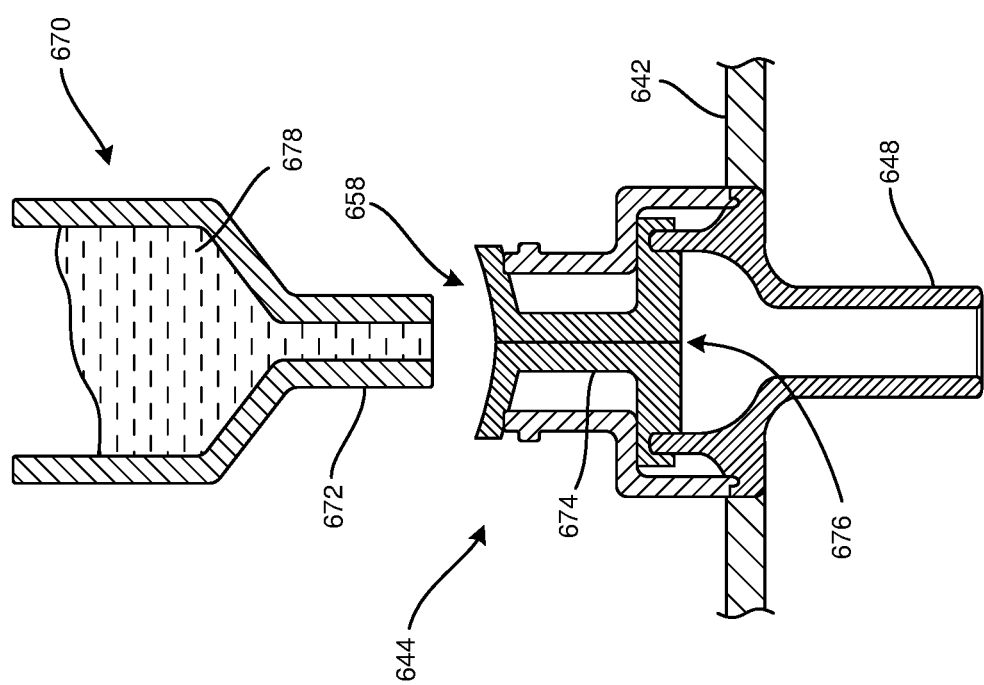
FIG. 6A is a side cross-sectional view of a needleless syringe and a needleless access port, with the needleless access port in a closed position, according to at least one embodiment of the present disclosure.
Figure 7:
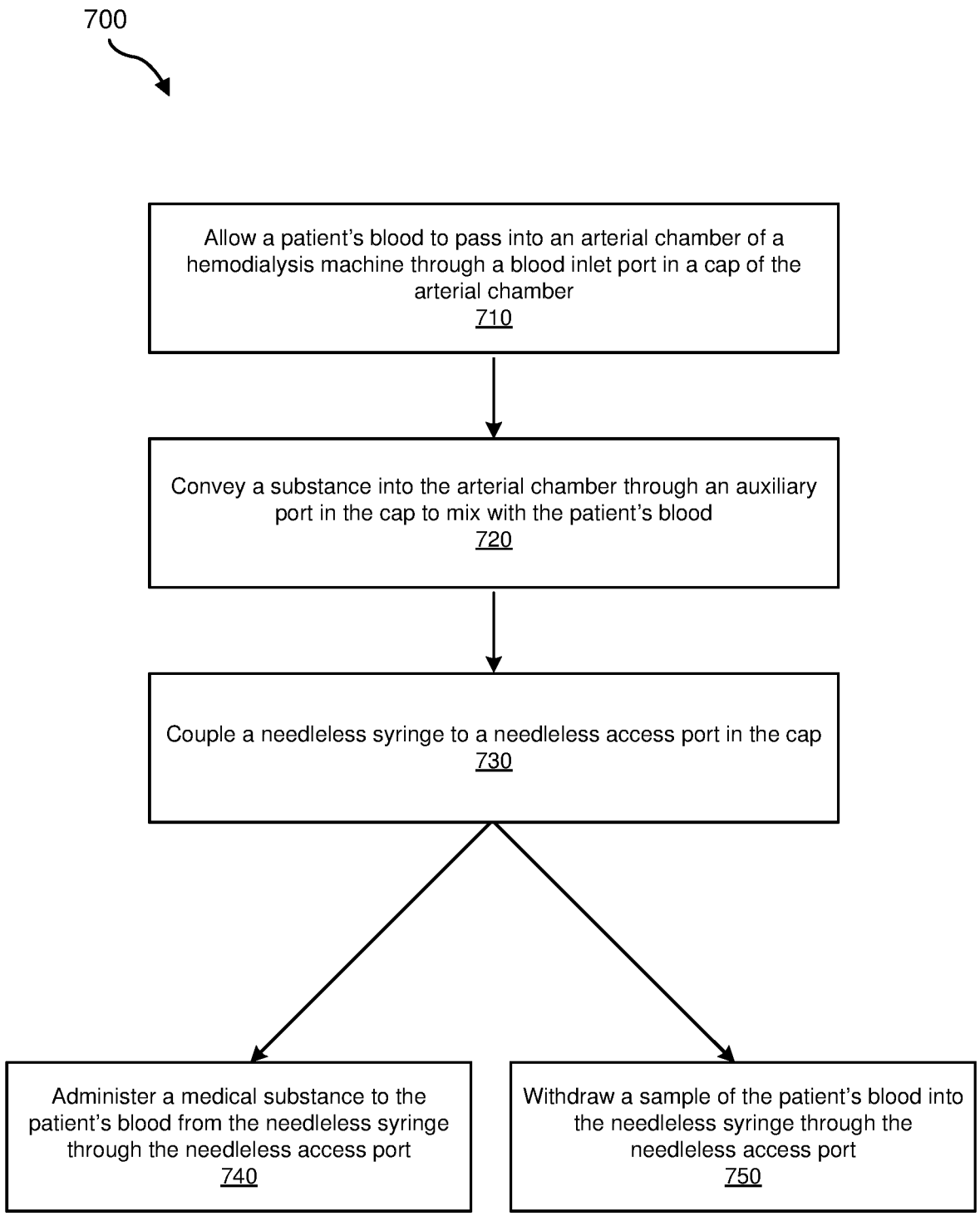
FIG. 7 is a flow diagram illustrating an example method for fluidically accessing an arterial chamber of a hemodialysis system, according to at least one embodiment of the present disclosure.

FIG. 6A is a side cross-sectional view of a needleless syringe 670 and a needleless access port 644, with the needleless access port 644 in a closed position, according to at least one embodiment of the present disclosure. FIG. 6B is a side cross-sectional view of the needleless syringe 670 and needleless access port 644 of FIG. 6A, with a shaft 672 of the needleless syringe 670 inserted into the needleless access port 644 and the needleless access port 644 in an open position. The needleless access port 644 may be rigidly coupled to a cap 642 of an arterial chamber of a hemodialysis system, as described above.

The needleless access port 644 may include a split septum 658 to maintain the needleless access port 644 in a closed position (FIG. 6A) when the needleless syringe 670 is decoupled from the needleless access port 644 and to allow for fluid to flow through the needleless access port 644 in an open position (FIG. 6B) when the needleless syringe 670 is coupled to the needleless access port 644. For example, the split septum 658 may include an elastomeric material 674 having at least one slit 676 therethrough. As shown in FIGS. 6A and 6B, a conduit 648 may extend into the arterial chamber from the needleless access port 644.

Referring to FIG. 6A, when the needleless access port 644 is in the closed position, the elastomeric material 674 of the split septum 658 may resiliently close the slit 676 to inhibit fluid flow through the split septum 658.

Referring to FIG. 6B, when the shaft 672 of the needleless syringe 670 is inserted into the needleless access port 644, the elastomeric material 674 of the split septum 658 may deform to resiliently open the slit 676 to accommodate the shaft 672 and to allow a substance 678 (e.g., a fluid, such as a medication, an anticoagulant, blood, saline solution, etc.) to flow through the split septum 658.

FIG. 7 is a flow diagram illustrating a method 700 for fluidically accessing an arterial chamber of a hemodialysis system. At operation 710, a patient's blood may be allowed to pass into an arterial chamber of a hemodialysis machine through a blood inlet port in a cap of the arterial chamber. Operation 710 may be performed in a variety of ways. For example, a pump (e.g., a roller-type pump) may be used to force the patient's blood into the arterial chamber. The patient's blood may be delivered to the blood inlet port in the cap of the arterial chamber by at least one flexible tube.

At operation 720, a substance may be conveyed into the arterial chamber through an auxiliary port in the cap to mix with the patient's blood. Operation 720 may be performed in a variety of ways. For example, a saline solution or an anticoagulant (e.g., heparin) may be allowed to flow into the arterial chamber through the auxiliary port as a result of gravity.

At operation 730, a needleless syringe may be coupled (e.g., fluidically coupled) to a needleless access port in the cap. Operation 730 may be performed in a variety of ways. For example, a shaft of the needleless syringe may be inserted into a split septum of the needleless access port to establish fluid communication between the needleless syringe and an interior of the arterial chamber.

At operation 740, a medical substance may be administered to the patient's blood within the arterial chamber from the needleless syringe through the needleless access port. Operation 740 may be performed in a variety of ways. For example, a medication, saline solution, or anticoagulant may be forced into the arterial chamber by a plunger of the needleless syringe.

Additionally or alternatively, after the needleless syringe is coupled to the needleless access port in the cap, at operation 750 a sample of the patient's blood may be withdrawn from the arterial chamber and into the needleless syringe (or into a different needleless syringe than may be used to administer a medical substance) through the needleless access port. Operation 750 may be performed in a variety of ways. For example, the patient's blood may be drawn through a conduit extending into the arterial chamber as a result of withdrawing a plunger of the needleless syringe.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. For example, the operation 720 of conveying the substance into the arterial chamber through the auxiliary port may be performed after any of the operations 730, 740, and/or 750. The various example methods described and/or illustrated herein may also omit one or more of the steps described or illustrated herein or include additional steps in addition to those disclosed.

Accordingly, the present disclosure includes arterial chambers, arterial-side tubing sets for hemodialysis, and related hemodialysis systems that may provide one or more improvements over conventional arterial chambers, arterial-side tubing sets for hemodialysis, and hemodialysis systems. For example, the arterial chambers of the present disclosure may include a housing, a blood outlet port, and a cap coupled to the housing. The cap may include at least three ports rigidly coupled to the cap, such as a blood inlet port, an auxiliary port, and a needleless access port. The needleless access port may facilitate administering a substance to an interior of the housing (e.g., to blood within the housing)

from a needleless syringe and/or withdrawing an intended patient's blood from the interior of the housing into the needleless syringe. The arterial chambers of the present disclosure improve fluidic access to blood within the arterial-side tubing sets of hemodialysis systems. In addition, the arterial chambers may reduce a risk of hazards associated with using needles to administer to or sample the blood being processed in hemodialysis systems.

The following example embodiments are also included in the present disclosure.

Example 1: An arterial chamber for hemodialysis, which may include: a housing defining an interior configured to collect air from an intended patient's blood passing through the housing; a blood outlet port for conveying the intended patient's blood out of the interior of the housing; and a cap coupled to the housing, the cap including: a blood inlet port for conveying the intended patient's blood into the interior of the housing; an auxiliary port configured to provide fluid access to the interior of the housing; and a needleless access port configured to couple to a needleless syringe for at least one of: administering a substance to the interior of the housing from the needleless syringe; or withdrawing the intended patient's blood from the interior of the housing into the needleless syringe.

Example 2: The arterial chamber of Example 1, wherein the needleless access port includes a split septum configured to open when a syringe shaft is inserted into the needleless access port and to close when the syringe shaft is withdrawn from the needleless access port.

Example 3: The arterial chamber of Example 1 or Example 2, wherein the needleless access port includes a Luer connection element for coupling a syringe to the needleless access port.

Example 4: The arterial chamber of any of Examples 1 through 3, wherein the needleless access port includes a conduit extending from the cap into the interior of the housing.

Example 5: The arterial chamber of Example 4, wherein the conduit extends from the cap to at least 25% of a height of the interior of the housing.

Example 6: The arterial chamber of Example 5, wherein the conduit extends from the cap to at least 50% of a height of the interior of the housing.

Example 7: The arterial chamber of any of Examples 1 through 6, wherein each of the blood inlet port, the auxiliary port, and the needleless access port is rigidly coupled to the cap.

Example 8: The arterial chamber of any of Examples 1 through 7, wherein the auxiliary port is configured for connection to an auxiliary element selected from the group consisting of: a saline solution source; an anticoagulant source; a pressure sensor; an air release valve; or a medication source.

Example 9: An arterial-side tubing set for a hemodialysis system, which may include: a first flexible tube configured to receive blood from an intended patient; an arterial chamber coupled to the first flexible tube and including a blood outlet port and a cap that includes: a blood inlet port configured to receive the blood from the first flexible tube and to convey the blood into an interior of the arterial chamber; an auxiliary port configured to provide fluid access to the interior of the arterial chamber; and a needleless access port configured to couple to a needleless syringe; and a second flexible tube coupled to the blood outlet port and configured to receive the blood from the interior of the arterial chamber.

Example 10: The arterial-side tubing set of Example 9, wherein the first flexible tube is configured to be operatively coupled to a pump for forcing the blood through the arterial-side tubing set.

Example 11: The arterial-side tubing set of Example 9, wherein the second flexible tube is configured to be operatively coupled to a pump for forcing the blood through the arterial-side tubing set.

Example 12: The arterial-side tubing set of any of Examples 9 through 11, wherein the needleless access port includes a split septum configured to open when a syringe shaft is inserted into the needleless access port and to close when the syringe shaft is withdrawn from the needleless access port.

Example 13: The arterial-side tubing set of any of Examples 9 through 12, wherein the blood inlet port, the auxiliary port, and the needleless access port are positioned in the cap in a triangular arrangement.

Example 14: A hemodialysis system, which may include: a dialyzer configured to withdraw at least one product from an intended patient's blood, the dialyzer including a dialyzer blood inlet, a dialyzer blood outlet, a dialysate inlet, and a dialysate outlet; an arterial-side tubing set fluidically coupled to the dialyzer blood inlet and configured to receive blood from the intended patient's artery, wherein the arterial-side tubing set includes an arterial chamber including a cap with an arterial chamber blood inlet port, an auxiliary port, and a needleless access port; and a venous-side tubing set fluidically coupled to the dialyzer blood outlet and configured to convey blood from the dialyzer to the intended patient's vein.

Example 15: The hemodialysis system of Example 14, wherein the venous-side tubing set includes a venous chamber including another cap with a venous chamber blood inlet port, another auxiliary port, and another needleless access port.

Example 16: The hemodialysis system of Example 14 or Example 15, further including a pump configured to force the intended patient's blood through the dialyzer, the arterial-side tubing set, and the venous-side tubing set.

Example 17: The hemodialysis system of any of Example 16, wherein the pump is coupled to the arterial-side tubing set downstream of the arterial chamber.

Example 18: The hemodialysis system of any of Example 16, wherein the pump is coupled to the arterial-side tubing set upstream of the arterial chamber.

Example 19: The hemodialysis system of any of Examples 14 through 18, wherein the arterial chamber includes an arterial drip chamber.

Example 20: The hemodialysis system of any of Examples 14 through 19, wherein each of the arterial chamber blood inlet port, auxiliary port, and needleless access port includes a respective conduit extending from the cap into an interior of the arterial chamber.

The preceding description has been provided to enable others skilled in the art to best utilize various aspects of the example embodiments disclosed herein. This example description is not intended to be exhaustive or to be limited to any precise form disclosed. Many modifications and variations are possible without departing from the spirit and scope of the present disclosure. The embodiments disclosed herein should be considered in all respects illustrative and not restrictive. Reference should be made to the appended claims and their equivalents in determining the scope of the present disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. An arterial chamber for hemodialysis, comprising:
   a housing defining an interior configured to collect air from an intended patient's blood passing through the housing;
   a blood outlet port for conveying the intended patient's blood out of the interior of the housing; and
   a cap coupled to a gravitational top of the housing, the cap comprising:
      a blood inlet port for conveying the intended patient's blood into the interior of the housing;
      an auxiliary port configured to provide fluid access to the interior of the housing; and
      a needleless access port comprising a conduit extending from the cap into the interior of the housing to at least 25% of a height of the interior of the housing, wherein a lower end of the conduit is lower than a lower end of the blood inlet port such that the lower end of the conduit is submerged in the patient's blood within the arterial chamber during operation, the needleless access port configured to couple to a needleless syringe for at least one of:
         administering a substance to the interior of the housing from the needleless syringe; or
         withdrawing the intended patient's blood from the interior of the housing into the needleless syringe.

2. The arterial chamber of claim 1, wherein the needleless access port comprises a split septum configured to open when a syringe shaft is inserted into the needleless access port and to close when the syringe shaft is withdrawn from the needleless access port.

3. The arterial chamber of claim 1, wherein the needleless access port comprises a Luer connection element for coupling a syringe to the needleless access port.

4. The arterial chamber of, claim 1, wherein the conduit extends from the cap to at least 50% of a height of the interior of the housing.

5. The arterial chamber of claim 1, wherein each of the blood inlet port, the auxiliary port, and the needleless access port is rigidly coupled to the cap.

6. The arterial chamber of claim 1, wherein the auxiliary port is configured for connection to an auxiliary element selected from the group consisting of:
   a saline solution source;
   an anticoagulant source;
   a pressure sensor;
   an air release valve; or
   a medication source.

7. An arterial-side tubing set for a hemodialysis system, the arterial-side tubing set comprising:
   a first flexible tube configured to receive blood from an intended patient;
   an arterial chamber coupled to the first flexible tube and comprising a blood outlet port and a cap at a gravitational top of the arterial chamber that includes:
      a blood inlet port configured to receive the blood from the first flexible tube and to convey the blood into an interior of the arterial chamber;
      an auxiliary port configured to provide fluid access to the interior of the arterial chamber; and
      a needleless access port comprising a conduit extending from the cap into the interior of the arterial chamber to at least 25% of a height of the interior of the arterial chamber, wherein a lower end of the conduit is lower than a lower end of the blood inlet port such that the lower end of the conduit is submerged in the patient's blood within the arterial chamber during operation, the needleless access port configured to couple to a needleless syringe; and
   a second flexible tube coupled to the blood outlet port and configured to receive the blood from the interior of the arterial chamber.

8. The arterial-side tubing set of claim 7, wherein the first flexible tube is configured to be operatively coupled to a pump for forcing the blood through the arterial-side tubing set.

9. The arterial-side tubing set of claim 7, wherein the second flexible tube is configured to be operatively coupled to a pump for forcing the blood through the arterial-side tubing set.

10. The arterial-side tubing set of claim 7, wherein the needleless access port comprises a split septum configured to open when a syringe shaft is inserted into the needleless access port and to close when the syringe shaft is withdrawn from the needleless access port.

11. The arterial-side tubing set of claim 7, wherein the blood inlet port, the auxiliary port, and the needleless access port are positioned in the cap in a triangular arrangement.

12. A hemodialysis system, comprising:
   a dialyzer configured to withdraw at least one product from an intended patient's blood, the dialyzer comprising a dialyzer blood inlet, a dialyzer blood outlet, a dialysate inlet, and a dialysate outlet;
   an arterial-side tubing set fluidically coupled to the dialyzer blood inlet and configured to receive blood from the intended patient's artery, wherein the arterial-side tubing set comprises an arterial chamber including a cap with an arterial chamber blood inlet port, an auxiliary port, and a needleless access port comprising a conduit extending from the cap into an interior of the arterial chamber to at least 25% of a height of the interior of the arterial chamber, wherein a lower end of the conduit is lower than a lower end of the blood inlet port such that the lower end of the conduit is submerged in the patient's blood within the arterial chamber during operation, wherein the cap is disposed at a gravitational top of the arterial chamber; and
   a venous-side tubing set fluidically coupled to the dialyzer blood outlet and configured to convey blood from the dialyzer to the intended patient's vein.

13. The hemodialysis system of claim 12, wherein the venous-side tubing set comprises a venous chamber including another cap with a venous chamber blood inlet port, another auxiliary port, and another needleless access port.

14. The hemodialysis system of claim 12, further comprising a pump configured to force the intended patient's blood through the dialyzer, the arterial-side tubing set, and the venous-side tubing set.

15. The hemodialysis system of claim 14, wherein the pump is coupled to the arterial-side tubing set downstream of the arterial chamber.

16. The hemodialysis system of claim 14, wherein the pump is coupled to the arterial-side tubing set upstream of the arterial chamber.

17. The hemodialysis system of claim 12, wherein the arterial chamber comprises an arterial drip chamber.

18. The hemodialysis system of claim 12, wherein each of the arterial chamber blood inlet port, auxiliary port, and needleless access port comprises a respective conduit extending from the cap into an interior of the arterial chamber.

\* \* \* \* \*